United States Patent [19]

Spector

[11] Patent Number: 4,889,286

[45] Date of Patent: Dec. 26, 1989

[54] CONTROLLABLE AIR FRESHENER UNIT

[76] Inventor: Donald Spector, 380 Mountain Rd., Union City, N.J. 07087

[21] Appl. No.: 245,693

[22] Filed: Sep. 19, 1988

[51] Int. Cl.$^4$ .............................................. A61L 9/12
[52] U.S. Cl. ........................................ 239/47; 239/57
[58] Field of Search ............................ 239/44–51.5, 239/53–60

[56] References Cited

U.S. PATENT DOCUMENTS

| | | | |
|---|---|---|---|
| 1,059,693 | 4/1913 | Woods | 239/57 X |
| 1,816,442 | 7/1931 | Reefer | 239/44 X |
| 1,818,684 | 8/1931 | Blickman | 239/44 X |
| 1,974,414 | 9/1934 | Dupuy | 239/45 X |
| 2,911,161 | 11/1960 | Skaist | 239/45 |
| 3,239,145 | 3/1966 | Russo | 239/58 X |
| 3,837,574 | 9/1974 | Curran | 239/57 |
| 4,283,011 | 8/1981 | Spector | 239/57 X |

FOREIGN PATENT DOCUMENTS 218892 4/1987 European Pat. Off. .............. 239/53

Primary Examiner—Robert J. Oberleitner
Assistant Examiner—Kevin P. Weldon
Attorney, Agent, or Firm—Michael Ebert

[57] ABSTRACT

A controllable air freshener unit in which a bottle filled with a volatile liquid fragrance is covered by a cap having vent holes therein that are covered by an absorbent membrane formed of microporous material disposed on the underside of the cap. When the bottle is placed in an upright position, the level of liquid is more or less below the cap and the membrane then acts as a barrier to prevent the discharge of fragrance vapor from the vented cap, the unit then being in its switched "off" state. When the bottle is placed in an inverted position raised above a supporting surface to expose the vented cap, the liquid then rests on the membrane and impregnates the pores thereof whereby a fragrance vapor is then wafted into the atmosphere and the unit is in its switched "on" state.

9 Claims, 2 Drawing Sheets

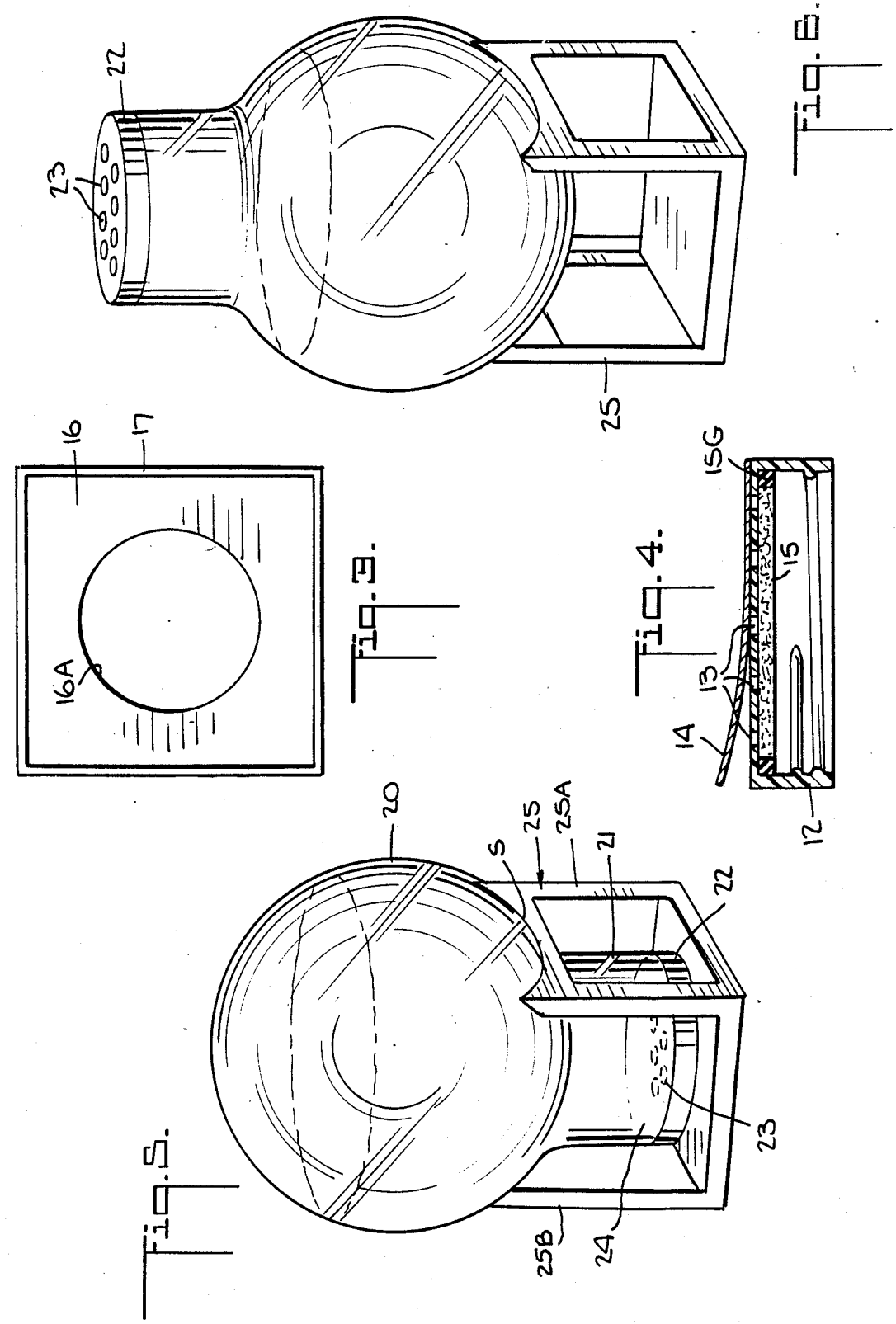

CONTROLLABLE AIR FRESHENER UNIT

BACKGROUND OF INVENTION

1. Field of Invention:

This invention relates generally to air freshener units which release an aroma into the atmosphere of a room or other enclosure, and more particularly to a wickless unit of this type which is controllable, whereby the unit, when it is in an upright position, is switched "off," and when the unit is in an inverted position, it is switched "on" to discharge a fragrance vapor into the atmosphere.

2. Status of Prior Art:

As used herein, the term "aroma" or "fragrance" is not limited to perfume-like odors, but encompasses any odor that is suitable as an air freshener to condition, modify or otherwise charge the ambient atmosphere.

The aroma of perfumes and perfume-based products such as colognes and toilets waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

One commercially well known air freshener unit is known as an "AIR-WICK," this unit including a wicking mechanism to draw an air-freshening liquid agent from a supply and to waft it into the atmosphere. Numerous methods have been devised which attempt to regulate the diffusion of volatile liquids with regard to the fragrancing or deodorization of an enclosure, such as those disclosed in U.S. Pat. Nos. 3,550,853; 3,804,331; 4,014,501 and 4,094,639.

The prior patent of greatest interest is U.S. Pat. No. 4,413,779 to Santini in which a bottle filled with liquid fragrance is provided with a removable stopper on which is mounted a porous plastic dome. A pair of rigid wicks extend from this dome through the stopper into the liquid bath whereby liquid is wicked from the bath into the absorbent dome and is volatilized from the surface of the dome.

In prior art freshener units of the AIR-WICK or Santini type which make use of wicks to draw liquid from a supply, it is relatively difficult to turn these units off to prevent the discharge into the atmosphere of a vapor when no need exists therefor. In a typical situation, it is desirable to render an air freshener unit operative only when the room is occupied and to turn it off when the room is unoccupied; for if the air freshener unit is on continuously day and night, it will be exhausted in a fairly short period.

While prior art units have in some instances a degree of control, as by retracting the wick mechanism, they cannot, unless motorized, simply be switched on and off.

SUMMARY OF INVENTION

In view of the foregoing, the main object of this invention is to provide an air freshener unit which is controllable simply by changing the position of the unit, so that when it is in an upright position, the unit is then switched "on" to discharge a vapor fragrance into the atmosphere, and when in an inverted position, the unit is switched "off."

More particularly, an object of this invention is to provide a controllable unit of the above type which is motorless and wickless and which contains a large supply of liquid fragrance whereby the unit has a prolonged operating life.

Also an object of this invention is to provide a unit of the above type constituted by a bottle filled with a volatile liquid fragrance and a stand therefor which functions to support the bottle in an upright switched "off" state or in an inverted switched "on" state. A significant feature of the invention is that the stand also functions as a packaging box for the bottle.

Briefly stated, these objects are attained in a controllable air freshener unit in which a bottle filled with a volatile liquid fragrance is covered by a cap having vent holes therein that are covered by an absorbent membrane formed of microporous material disposed on the underside of the cap. When the bottle is placed in an upright position, the level of liquid is more or less below the cap and the membrane then acts as a barrier to prevent the discharge of fragrance vapor from the vented cap, the unit then being in its switched "off" state. When the bottle is placed in an inverted position raised above a supporting surface to expose the vented cap, the liquid then rests on the membrane and impregnates the pores thereof whereby a fragrance vapor is then wafted into the atmosphere and the unit is in its switched "on" state.

BRIEF DESCRIPTION OF DRAWINGS

For a better understanding of the invention as well as other objects and further features thereof, reference is made to the following detailed description to be read in conjunction with the accompanying drawings, wherein:

FIG. 3 shows the underside of the unit;

FIG. 4 is a section taken through the cap of the unit;

FIG. 5 is a perspective view of another embodiment of a controllable air freshener unit in accordance with the invention in its switched "off" state; and FIG. 6 shows the unit in its switched "on" state.

DESCRIPTION OF INVENTION

Figure 2:
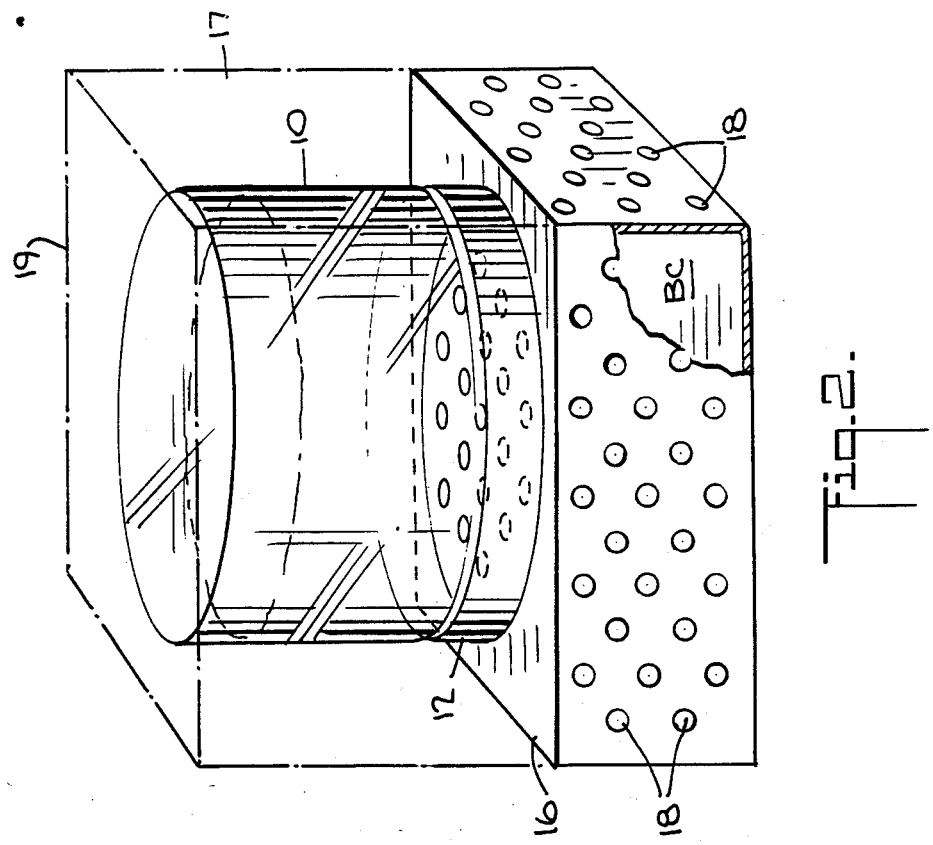
FIG. 2 shows the unit in its switched "on" state.

First Embodiment:

Referring now to FIGS. 1 to 4, there is shown an air freshener unit in accordance with the invention, the unit including a jar or bottle 10 formed of glass or rigid, synthetic, plastic material such as polyethylene. Bottle 10 is filled with a volatile liquid fragrance appropriate to the end use of the unit.

Bottle 10 is provided with a removable cap 12 which in practice may be of the screw-in type, in which case the mouth of the bottle is threaded to receive the cap. Cap 12 is provided with an array of vent holes 13, the upper surface being covered with a removable seal 14 to prevent any loss of liquid during storage and shipment. Seal 14 is in the form of a sheet of impermeable, flexible film material having a low-tack, pressure-sensitive adhesive layer on its undersurface, making it possible to peel off the seal and to expose vent holes 13 when the unit is put to use.

Fitting against the underside of the cap and covering vent holes 13 is a disc-shaped membrane 15 of absorbent, microporous material held within a ring-shaped gasket 15G of compressible material. This gasket is engaged by the rim of the bottle when the cap is screwed in place. Membrane 15 is preferably formed of TESLIN, a synthetic plastic printing sheet material manufactured and marketed by PPG (Pittsburgh Plate Glass Industries of Barbertown, Ohio).

TESLIN is a single layer, totally synthetic, microporous material composed primarily of polyethylene. Its physical properties are unaffected by water or by liquid fragrances. TESLIN is chemically non-reactive to standard liquid oil-based fragrances. The invention is not limited to TESLIN, for membrane 15 may be composed of any absorbent, synthetic, plastic material of polyethylene, polyurethane or other material which is microporous and is inert with respect to the liquid fragrance.

Bottle 10 is seated on a platform 16 formed within a closed box 17 above the base thereof, platform 16 having a circular opening 16A therein providing access to a base chamber BC. The sides of base chamber BC are provided with vent holes 18. Box 15 is provided with a top 19 formed of suitable closure flaps so that the box can be opened to obtain access to the bottle housed therein. These flaps are provided with perforations at their fold lines so that they can be torn off after the top is opened.

Figure 1:
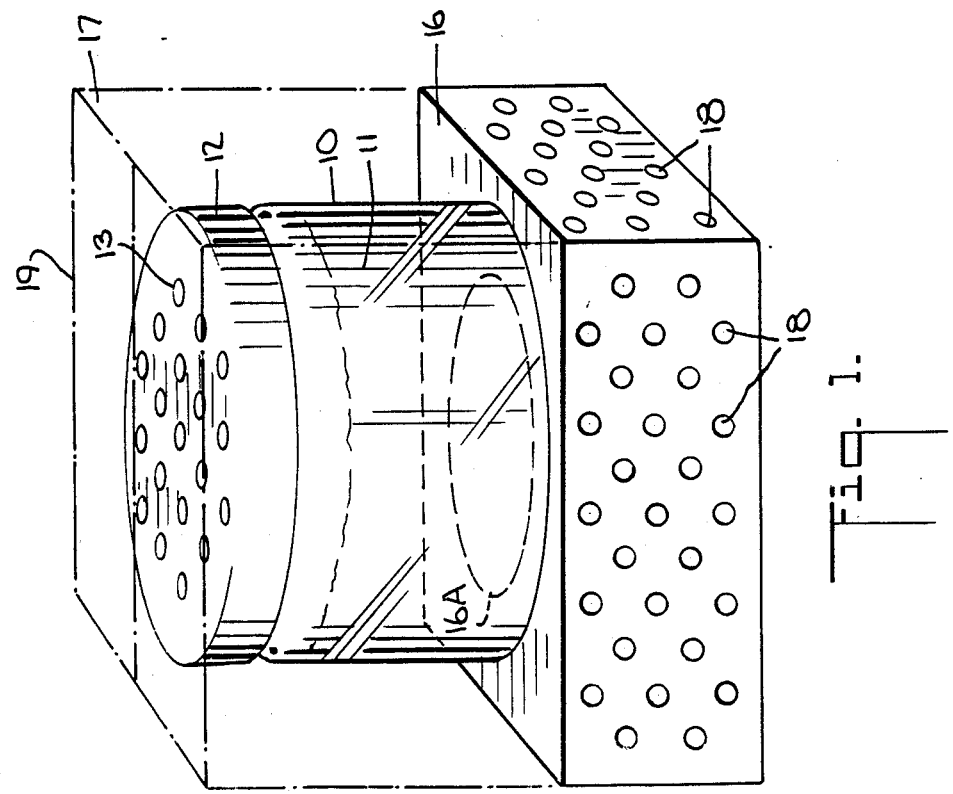
FIG. 1 is a perspective view of one embodiment of a controllable air freshener unit in accordance with the invention in its switched "off" state.

When the unit is in its "off" state, as shown in FIG. 1, bottle 10 is then upright with its bottom resting over opening 16A in platform 16, cap 12 being then just below the top 19 of the box. The level of liquid fragrance 11, even when the bottle is full, is somewhat below membrane 15 which then acts as a barrier to prevent the escape of fragrance vapor from the bottle through vent holes 13 in the cap.

In order to switch "on" the unit, the bottle is inverted, as shown in FIG. 2, so that now cap 12 overlies the opening 16A in platform 16 and liquid fragrance 11 rests on microporous membrane 15 which then slowly absorbs and becomes impregnated with the liquid. Because the pores in the membrane are microscopic, the liquid does not leak through the membrane but is retained in the pores. However, fragrance vapor volatilized from the surface of the membrane in contact with the underside of cap 12 then is exuded through cap vents 13 into base chamber BC and from there through the vents 18 into the atmosphere.

The unit is shipped and stored with the bottle in the closed box in its upright "off" position. The user of the unit opens the top of the box, removes the bottle therefrom and then peels off seal 14 to expose vent holes 13 in cap 12. He then returns the bottle to the now open box in the inverted position shown in FIG. 2, with the cap now resting on platform 16 over platform opening 16A. The unit is now in the switched "on" state to exude a fragrance vapor into the atmosphere. When the user wishes to switch "off" the unit, he simply takes the inverted bottle out of the box and returns it to its upright FIG. 1 position. In this way, fragrance is conserved for the unit is only active when switched "on" and when there is no need for fragrance, it is a simple matter to switch the unit "off."

Second Embodiment:

In the arrangement shown in FIGS. and 6, the bottle 20 which is filled with a volatile liquid fragrance is generally spherical in form and is provided with a cylindrical throat 21 covered by a removable cap 22 having an array of vent holes 23. Cap 22 is essentially the same as cap 12 in the first embodiment and is provided with a microporous absorbent membrane 24.

Also provided is a bottle stand which may be formed of plastic or cardboard, generally designated by numeral 25. The stand includes a pair of vertical frame members 25A and 25B which are spaced apart by a distance somewhat smaller than the diameter of the bottle, each having an arcuate seat S to accommodate the spherical bottle. The stand supports the bottle so that in its inverted position, as shown in FIG. 5, cap 22 is then raised somewhat above the surface on which the stand rests to expose vent holes 23 in the cap. In this inverted position, the unit is in its switched-on state.

In order to turn off the unit, the spherical bottle is placed on the stand in an upright position, as shown in FIG. 6. In this position, the liquid level is below cap 22 and membrane 24 then acts as a barrier to prevent the discharge of liquid vapor into the atmosphere. This barrier action takes place only after the membrane is dry.

That is to say, when the bottle is inverted as in FIG. 5, then the liquid rests on membrane 23 and impregnates the pores thereof, and as liquid from the pores is volatilized and discharged into the atmosphere, the pores are replenished with liquid so that the unit remains switched on as long as there is liquid in the bottle. But when the bottle is upright, the pores of the membrane are not replenished with liquid, and when the liquid in the pores is exhausted and the membrane is dry, the unit turns off.

A degree of control in regard to the rate of fragrance vapor emission can be effected with the unit shown in FIGS. 5 and 6 by orienting the bottle on the stand so that it is not inverted, as shown in FIG. 5, with its axis vertical, but with its axis inclined from the vertical, in which case the liquid pressure imposed on the membrane is not as great as that attained with vertical orientation. Thus, the emission is smaller when the inclination is 45 degrees from vertical than when 20 degrees therefrom.

While there have been shown and described preferred embodiments of a decorative air freshener unit in accordance with the invention, it will be appreciated that many changes and modifications may be made therein without, however, departing from the essential spirit thereof.

I claim:

1. A wickless controllable air freshener unit comprising:
   (A) a bottle filled with a liquid fragrance and provided with a cap thereon having vent holes therein;
   (B) a membrane formed of microporous material, disposed on the underside of the cap to cover the vent holes; and
   (C) a stand supporting said bottle above the surface on which the stand is placed in either an upright position in which the level of liquid in the bottle is below the membrane which then acts as a barrier to prevent vapor emitted from the liquid fragrance from passing through the vent holes, in which state the unit is turned off, or in an inverted position in which the liquid rests on the membrane and the cap is raised above said surface, the membrane then becoming impregnated with the liquid which is volatilized from the membrane to produce a vapor that is exuded into the atmosphere through the cap vent holes, in which state the unit is turned on whereby a user may turn the unit on or off simply by changing the bottle position on the stand.

2. A unit as set forth in claim 1, in which the membrane is supported within a gasket ring that is compressed when the cap is on the bottle.

3. A unit as set forth in claim 1, wherein said cap is removable and is threadably received on the mouth of the bottle.

4. A unit as set forth in claim 1, wherein said membrane is formed primarily of polyethylene.

5. A unit as set forth in claim 1, wherein said stand is constituted by a box having a top, a base and a platform above the base to define therewith a base chamber having side vent openings therein, said platform having an opening therein on which the cap rests in the "on" state of the unit.

6. A unit as set forth in claim 5, wherein said box top is formed by closure flaps which are removable from the box to permit the escape of vapor into the atmosphere.

7. A unit as set forth in claim 1, wherein said cap is provided at its upper side with a peel-off seal.

8. A unit as set forth in claim 1, wherein said bottle is generally spherical and is provided with a cylindrical throat on which said cap is placed.

9. A unit as set forth in claim 8, wherein said stand is provided with a seat to support said spherical bottle in a position raised above the surface on which the stand is placed so that in its inverted position, the cap is above the surface.

* * * * *